US00PP08867P

United States Patent [19]

Viette

[11] Patent Number: Plant 8,867

[45] Date of Patent: Aug. 23, 1994

[54] RUDBECKIA PLANT NAMED VIETTE'S LITTLE SUZY

[76] Inventor: Mark A. Viette, Rte. 1, Box. 25B, Fishersville, Va. 22939

[21] Appl. No.: 101,359

[22] Filed: Aug. 3, 1993

[51] Int. Cl.[5] ..... A01H 5/00

[52] U.S. Cl. ..... Plt./68.1

[58] Field of Search ..... Plt. 68.1

[56] References Cited

PUBLICATIONS

Huxley, A., et al., (Eds.) "Rudbeckia", *The New RHS Dictionary of Gardening* 4 Stockton Press (1992) N.Y., pp. 145–146.

*Primary Examiner*—James R. Feyrer

*Attorney, Agent, or Firm*—Foley & Lardner

[57] ABSTRACT

A rudbeckia fulgida var. speciosa plant named Viette's Little Suzy, characterized by its dwarf habit, having a total plant height of only 14 inches, approximately one-half the typical height of plants of this species, bright yellow orange ray florets and a domed dark purple center, very floriferous habit; and dark green foliage which fades to a dark grayed-purple during cooler temperatures and after frost.

1 Drawing Sheet

1

The present application comprises a new and distinct cultivar of *Rudbeckia fulgida* var. speciosa known by the cultivar name Viette's Little Suzy.

The genus Rudbeckia, also commonly known as coneflower, is comprised of more than 25 species of perennial, annual and biennial herbs characterized generally by their relatively tall, long-stemmed habit with typically daisy-like flowers comprised of yellow ray florets and a raised center formed by dark brown, purplish or black disk florets. The species fulgida var. speciosa is a perennial which grows to three (3) feet tall, has lance-shaped leaves up to six (6) inches long, yellow ray florets, flower diameter of approximately 3–4 inches, and dark purplish disk florets.

The new cultivar Viette's Little Suzy is a mutation or sport of an unnamed and unpatented plant of *R. fulgida* var. speciosa, and was discovered and selected by the inventor Mark A. Viette in a cultivated area in Fishersville, Va. in June 1990. The new cultivar located in a cultivated area was growing in a bed of plants of its parent cultivar, and was immediately recognized due to its dwarf habit.

The mutation was first asexually propagated or reproduced in Fishersville, Va. in July 1990 by the inventor Mark A. Viette by taking stem cuttings. That and subsequent generations of asexual reproduction have clearly established that the combination of characteristics as herein disclosed for Viette's Little Suzy are firmly fixed and are retained through successive generations of asexual reproduction.

Viette's Little Suzy has not been observed under all possible environmental conditions. The phenotype may vary with variations in environment such as temperature, light intensity, etc. without, however, any variation in genotype. The following observations, measurements and comparisons describe plants grown in Fishersville, Va. under conditions which approximate those generally used in commercial practice.

The following traits have been repeatedly observed and are determined to be basic characteristics of Viette's Little Suzy, which in combination distinguish this Rudbeckia plant as a new and distinct cultivar.

1. The overall height of Viette's Little Suzy averages only approximately 14 inches, as opposed to a typical height of approximately 28 inches or more for plants of

2 the indicated species, including the parent cultivar from which the new cultivar mutated.

2. The leaves are shorter than the leaves of the parent cultivar and other known plants of the species, and the overall height of the foliage is only approximately 5–8 inches above ground level, or above the top of the pot for pot grown plants. The dwarf habit essentially maintains the proportion of foliage height to total plant height.

3. The ray florets of Viette's Little Suzy are bright yellow with the center of the flower being domed and comprised of disc florets dark purple in color. The overall flower diameter for a mature flower is approximately two (2) inches, slightly less than mature flower diameters of the parent and other plants of its species. The cultivar is very floriferous.

4. The foliage color of the new cultivar is dark green for mature foliage, turning to a dark grayed-purple in the fall, apparently due to cooler temperatures. This color change is not expressed in the parent or other plants of this species.

5. The dwarf habit of the new cultivar produces a very showy plant in that its floriferousness tends to be relatively more prominent than the foliage which is of substantially reduced height. The new cultivar is particularly useful for growing as a perennial bedding plant. In Virginia, the plant is in bloom from June until frost.

To the best knowledge of applicant, there is no known cultivar with which Viette's Little Suzy can be meaningfully compared. Although the new cultivar is similar to plants of *R. fulgida* var. speciosa with respect to yellow ray floret color, flowering all summer, and hardiness, its dwarf compact habit make the new cultivar truly unique among varieties comprising this species.

The accompanying color photographic drawings show typical inflorescence and foliage characteristics of Viette's Little Suzy, with colors being as nearly true as possible with illustrations of this type. The photograph at the top of the sheet comprises a top perspective view of a specimen plant of the new cultivar grown in a 6-inch pot, with a ruler in inches also appearing in the photo. The photo at the bottom comprises a slightly enlarged close-up view of several flowers.

The photos are of a plant approximately two years old and forced into flowering in a greenhouse in order to obtain photographs for patent application purposes. However, the described charcteristics are the same for greenhouses or outdoor culture, with the only difference in growth of the new cultivar in the respective environments being that when forced in a greenhouse, flowering begins approximately one month earlier, in mid to late May.

Classification:

*Botanical.*—*Rudbeckia fulgida* var. speciosa.

*Commecial.*—Dwarf rudbeckia, cv. Viette's Little Suzy.

INFLORESCENCE

A. Capitulum:

*Form.*—Daisy.

*Type.*—Flat.

*Diameter across face.*—1.5 to 2 inches for mature flowers. Parent cultivar is somewhat larger, approximately 2 to 3 inches.

B. Corolla of ray florets:

*Color (general tonality from a distance of three meters).*—Bright yellow orange.

*Color (upper surface).*—Approximately 21A.

*Color (under surface).*—Approximately 12A infused with 154A.

*Size.*—Mature florets are approximately 1 1 inch in length and 0.25 inch in width at widest point.

*Shape.*—Generally elliptical, with notched tip.

*Number.*—There are 21 petals.

C. Corolla of disc florets:

*Color (mature).*—Approximately 187A.

*Diameter.*—Approximately 0.7 inch.

*Depth.*—Approximately 0.3–0.4 inch.

D. Reproductive organs:

*Androecium.*—Present on disc florets only pollen yellow in color.

*Gynoecium.*—Present on both ray and disc florets.

E. Flower stems: The flower stem length is approximately 10–12 inches from ground to bloom, compared to 24–26 inches for the parent cultivar when similarly measured.

PLANT

A. General appearance: The dwarf habit produces a very low and compact, yet full and symmetrical plant. The floriferous habit with the relatively large flowers compared to the greatly reduced overall height of the plant produces a very showy plant when in bloom.

*Height.*—The total height of the plant (from ground or top of pot to top of flowers) is approximately 14 inches, approximately one-half the typical plant height (28 inches) of the parent and other plants of this species. Of the total height, the foliage is only approximately 5–8 inches, thereby more prominently displaying flowering.

*Diameter.*—The diameter or spread for a one year old plant is approximately 12–14 inches at peak flowering. The parent has a spread of approximately 14–24 inches for a plant of the same age.

B. Foliage (mature):

*Color (upper surface).*—Between 137A and 139A, fading non-uniformly to a dark greyed-purple, approximately 187B-C.

*Color (under surface).*—Closest to 147B.

*Shape.*—Elliptical and elongated, with acute base and tip; concave when opening, becoming generally flat when mature.

*Aspect.*—Hairy.

*Size.*—Approximately 3–4 inches in length and 1.25–1.5 inches in width at widest point.

*Leaf stem.*—Up to 100 mm in length, approximately 146C in color.

*Veins.*—On underside of leaf, approximately 146C.

I claim:

1. A new and distinct cultivar of Rudbeckia plant named Viette's Little Suzy, as illustrated and described.

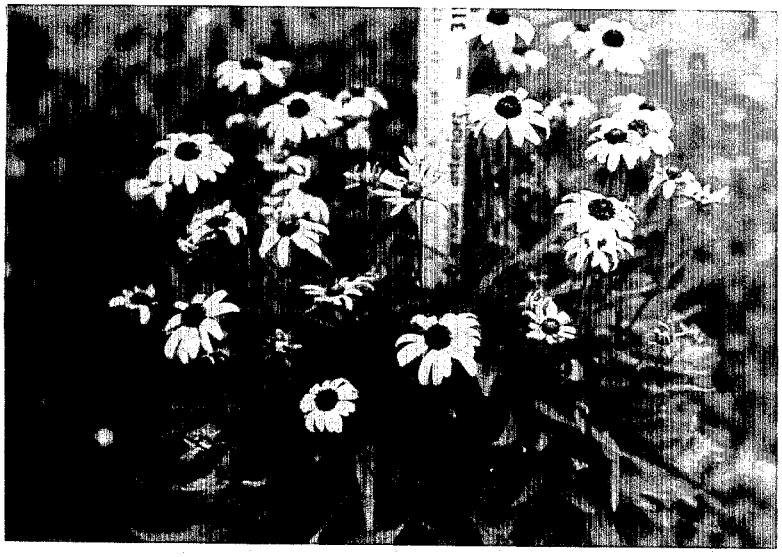
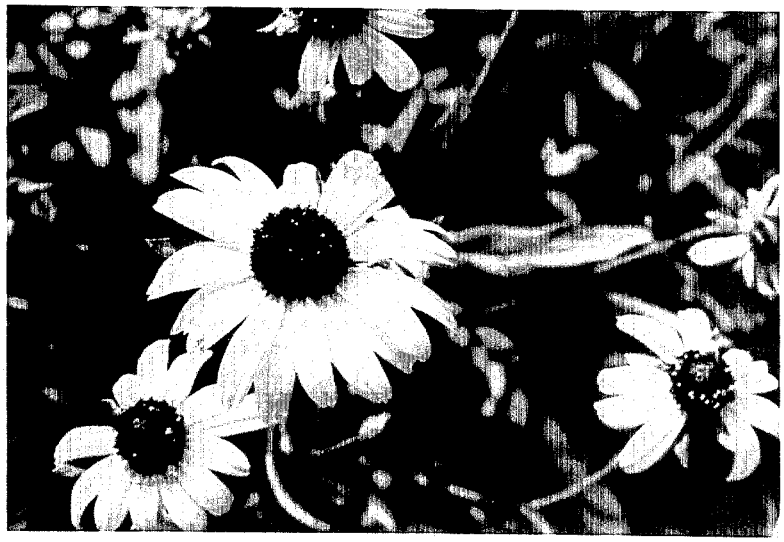

* * * * *